US011518600B2

(12) United States Patent
Robinson et al.

(10) Patent No.: US 11,518,600 B2
(45) Date of Patent: Dec. 6, 2022

(54) INTERFACE/POUCH DESIGN FOR ASEPTIC OPENING OF STERILIZATION POUCH

(71) Applicant: American Sterilizer Company, Mentor, OH (US)

(72) Inventors: Nancy A. Robinson, Fernandina Beach, FL (US); Janet E. Meszaros, Willowick, OH (US)

(73) Assignee: American Sterilizer Company, Mentor, OH (US)

( * ) Notice: Subject to any disclaimer, the term of this patent is extended or adjusted under 35 U.S.C. 154(b) by 226 days.

(21) Appl. No.: 16/992,367

(22) Filed: Aug. 13, 2020

(65) Prior Publication Data
US 2021/0292072 A1 Sep. 23, 2021

Related U.S. Application Data

(60) Provisional application No. 62/993,316, filed on Mar. 23, 2020.

(51) Int. Cl.
*B65D 81/18* (2006.01)
*B65D 33/01* (2006.01)
(Continued)

(52) U.S. Cl.
CPC .............. *B65D 81/18* (2013.01); *A61B 50/30* (2016.02); *B65D 33/01* (2013.01); *B65D 33/18* (2013.01); *A61B 2050/314* (2016.02)

(58) Field of Classification Search
CPC ......... B65D 81/18; B65D 33/01; B65D 33/18
(Continued)

(56) References Cited

U.S. PATENT DOCUMENTS 3,604,616 A * 9/1971 Greif ............... A61B 50/30
206/439
3,685,720 A 8/1972 Brady
(Continued)

FOREIGN PATENT DOCUMENTS

EP         1 033 238 A1    9/2000
JP       2006/347615 A    12/2006
(Continued)

OTHER PUBLICATIONS

Cheng et al., "Measuring and Contrastive Analysis of Two Kinds of Sterilization Packaging of Surgical Instruments," International Conference on Smart Grid and Electrical Automation (ICSGEA), IEEE, pp. 403-405, May 2017.

(Continued)

*Primary Examiner* — Jacob K Ackun
(74) *Attorney, Agent, or Firm* — Kusner & Jaffe

(57) ABSTRACT

A sterilizable pouch includes at least one sheet, wherein outer peripheral edges of the at least one sheet are sealed together to define a pouch having an interior space for receiving an article therein. A first releasable seam spans between a first peripheral edge of the at least one sheet to a second, opposite, peripheral edge of the at least one sheet, the first releasable seam dividing the at least one sheet into a first sheet part and a second sheet part. A second releasable seam and a third releasable seam each substantially span from a third peripheral edge of the at least one sheet to a fourth, opposite, peripheral edge of the at least one sheet and along the first peripheral edge and the second peripheral edge, respectively. The second and third releasable seams are arranged generally perpendicular to the first releasable seam, where the first, second and third releasable seams enable the pouch to be completely opened such that a device
(Continued)

can be removed from the pouch without the device contacting non-sterile portions of the pouch.

21 Claims, 8 Drawing Sheets

(51) Int. Cl.
*A61B 50/30* (2016.01)
*B65D 33/18* (2006.01)

(58) Field of Classification Search
USPC .................................................. 383/210, 41
See application file for complete search history.

(56) References Cited

U.S. PATENT DOCUMENTS

| | | | |
|---|---|---|---|
| 3,754,700 A | 8/1973 | Bonk | |
| 3,761,013 A | 9/1973 | Schuster | |
| 3,768,725 A * | 10/1973 | Pilaro | A61B 50/30 206/439 |
| 4,057,144 A | 11/1977 | Schuster | |
| 4,264,392 A * | 4/1981 | Watt | B29C 66/432 156/244.11 |
| 4,279,344 A * | 7/1981 | Holloway, Jr. | B65D 75/26 229/123.1 |
| 4,395,254 A | 7/1983 | Schuster | |
| 4,496,046 A | 1/1985 | Stone et al. | |
| 4,936,456 A * | 6/1990 | Bell | B65D 33/00 206/439 |
| 5,253,754 A * | 10/1993 | Soodak | A01N 1/0268 493/189 |
| 5,415,904 A * | 5/1995 | Takubo | B65D 33/2541 24/585.12 |
| 5,688,476 A * | 11/1997 | Bourne | B32B 7/05 206/439 |
| 5,715,943 A * | 2/1998 | Thompson, Jr. | A61L 2/26 206/439 |
| 6,406,764 B2 * | 6/2002 | Bayer | A61L 2/26 422/26 |
| 2003/0123759 A1 * | 7/2003 | Banks | B65D 27/22 383/88 |
| 2011/0033137 A1 * | 2/2011 | Gaynor | B65D 65/22 383/105 |
| 2014/0133785 A1 | 5/2014 | Diviesti et al. | |

FOREIGN PATENT DOCUMENTS

| | | |
|---|---|---|
| JP | 2015/195963 A | 3/2018 |
| WO | WO 2019/208628 A1 | 10/2019 |

OTHER PUBLICATIONS

International Search Report and Written Opinion issued in related International Application No. PCT/US2021/021472 dated Jun. 14, 2021.

* cited by examiner

INTERFACE/POUCH DESIGN FOR ASEPTIC OPENING OF STERILIZATION POUCH

RELATED APPLICATIONS

This application claims the benefit of U.S. Provisional Application No. 62/993,316 filed Mar. 23, 2020, which is hereby fully incorporated herein by reference.

FIELD OF THE INVENTION

The invention pertains to sterilization pouches for packaging items for sterilizing and then storing medical articles after being sterilized and, more particularly, to an opening means for a sterilization pouch that can be opened such that an article stored within the pouch can be removed while reducing risk of contacting non-sterile portions of the pouch.

BACKGROUND OF THE INVENTION

Conventionally there are three methods in which a sterilization pouch is sealed. A first method involves the use of self-sealing tape. In this regard, the tape may be part of the pouch design or may be attached to the pouch just prior to sealing. A second method involves the use of a heat seal (also referred to as a hot seal). In a heat seal, the two pouch layers near the open end may be sealed by applying concentrated heat to the area to cause the two surfaces to fuse together and create a seal. A third method simply rolls the open end and then tape is applied to prevent unrolling.

To open the pouch and remove an article stored in the pouch, a user typically peals apart the two materials forming the seal. However, it is difficult for a user to aseptically peal open a long self-seal/heat seal pouch that is used to enclose larger objects, such as a sterilization tray. For example, the pouch can shear through the material rather than peal apart, which can cause the non-sterile pouch outer surface of the pouch to touch the tray and thus contaminate the tray. Also, the user's arms may not be long enough to peal the entire length of the pouch aseptically. For example, the user may lose control of the pouch material and nonsterile parts of the pouch may touch the tray. Further, when using a rolled seal two individuals may be required to move the tray aseptically (e.g., one (non-sterile) individual to open the rolled end and then hold the end of the pouch so that the sterile individual can reach inside and remove the tray).

SUMMARY OF THE INVENTION

A device and method in accordance with the present invention enable a user to aseptically open a pouch from a central region of the pouch or the central region of an object stored in the pouch (e.g., a tray) rather than an end of the pouch/end of the object in the pouch. The opening region can be part of a pre-formed opening means of the pouch, the opening means providing a region adjacent to a peal-open seam for the user to grasp. The opening means may be composed of materials that can be sealed in a manner that the seal remains closed when the pouch is subjected to normal handling, and yet can be opened for retrieving sterilized items without compromising aseptic presentation.

In one embodiment, a portion of the pouch may be formed from a breathable (e.g., fibrous) material, such as paper or Tyvek® plastic sheet, which enables sterilization medium to pass there through. The remaining portion may be formed from a thin non-fibrous plastic sheet material and bonded to the fibrous material along the outer peripheral edges of the fibrous and non-fibrous sheet material. The pouch includes an opening means located in the central region of the pouch, the region formed as two pieces. Each piece can be grasped by one hand and pulled in opposite directions, thereby completely opening the pouch such that the device contained in the pouch can be lifted out with reduced risk of contacting exterior (non-sterile) surfaces of the pouch. The opening means may include fibrous strips (e.g., paper or Tyvek® plastic strips) arranged across the central region, and small paper or Tyvek® plastic strips extending to the sides of the opening means. In another embodiment, the opening means may be formed as a "zip lock" seal that can be opened by applying a pulling force.

An advantage of the device and method in accordance with the invention is that the central location of the opening means decreases the distance the user must extend his/her arms when opening the pouch. The shorter expanse allows the user to maintain control of the materials, preventing the non-sterile outside portions of the pouch from touching the enclosed object. Thus, the central location allows the user to easily open the pouch containing the tray aseptically.

According to one aspect of the invention, a sterilizable pouch includes: a first sheet; a second sheet, wherein outer peripheral edges of the first and second sheets are sealed together to define a pouch having an interior space for receiving an article therein; a first releasable seam spanning between a first peripheral edge of the first sheet to a second, opposite, peripheral edge of the first sheet, the first releasable seam dividing the first sheet into a first sheet part and a second sheet part; and a second releasable seam and a third releasable seam each substantially spanning from a third peripheral edge of the first sheet to a fourth, opposite, peripheral edge of the first sheet and along the first peripheral edge and the second peripheral edge, respectively, the second and third releasable seams arranged generally perpendicular to the first releasable seam, where the first, second and third releasable seams enable the pouch to be completely opened such that a device can be removed from the pouch without the device contacting non-sterile portions of the pouch.

In one embodiment, the first and second sheets are joined together along outer peripheral edges of the respective sheets to define the pouch.

In one embodiment, the first and second sheet parts have approximately the same surface area.

In one embodiment, the first releasable seam bisects one of the first sheet.

In one embodiment, a surface area of the first sheet part is at least one third of a surface area of the second sheet part.

In one embodiment, at least one of the first sheet or the second sheet comprises a breathable material.

In one embodiment, the breathable material comprises a fibrous material.

In one embodiment, the fibrous material comprises an uncoated fibrous material.

In one embodiment, the breathable material is impervious to microorganisms and pervious to gases.

In one embodiment, at least one of the first, second or third releasable seam comprises a mating male rib and a female sealing closure.

In one embodiment, at least one of the first, second or third releasable seam comprises a paper seam.

In one embodiment, at least one of the first, second and third releasable seam comprises a layer of fibrous material arranged between two layers of plastic film.

In one embodiment, at least one of the first, second or third releasable seam comprises a heat-sealed portion.

In one embodiment, at least one of the first, second or third releasable seam comprises adhesive tape.

In one embodiment, one of the first sheet or the second sheet comprises a non-breathable flexible film.

In one embodiment, the non-breathable flexible film comprises low density polyethylene plastic.

In one embodiment, at least one of the second and third releasable seam comprises a grasping portion for pulling apart at least one of the first, second or third releasable seam.

In one embodiment, the pouch comprises gussets.

According to another aspect of the invention, a sterilizable pouch includes: a first outer surface; a second outer surface arranged opposite the first outer surface, the second outer surface joined to the first outer surface along peripheral edges of the first and second outer surfaces to define an interior space for storing an article; a first releasable seam spanning between a first peripheral edge and a second peripheral edge of one of the first outer surface or the second outer surface, the first releasable seam dividing one of the first outer surface or the second other surface into a first part and a second part, wherein a surface area of the first part and the second part are substantially equal to each other; and at least one second releasable seam substantially spanning between a third peripheral edge and a fourth, opposite peripheral edge of one of the first outer surface or the second outer surface and along at least one of the first peripheral edge or the second peripheral edge, the at least one second releasable seam arranged generally perpendicular to the first releasable seam, where the first and at least one second releasable seams enable the pouch to be completely opened such that an article stored in the interior space can be removed without the device contacting non-sterile portions first or second outer surfaces.

According to another aspect of the invention, a sterilizable pouch includes: at least one sheet, wherein outer peripheral edges of the at least one sheet are sealed together to define a pouch having an interior space for receiving an article therein; a first releasable seam spanning between a first peripheral edge of the at least one sheet to a second, opposite, peripheral edge of the at least one sheet, the first releasable seam dividing the at least one sheet into a first sheet part and a second sheet part; and a second releasable seam and a third releasable seam each substantially spanning from a third peripheral edge of the at least one sheet to a fourth, opposite, peripheral edge of the at least one sheet and along the first peripheral edge and the second peripheral edge, respectively, the second and third releasable seams arranged generally perpendicular to the first releasable seam, where the first, second and third releasable seams enable the pouch to be completely opened such that a device can be removed from the pouch without the device contacting non-sterile portions of the pouch.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
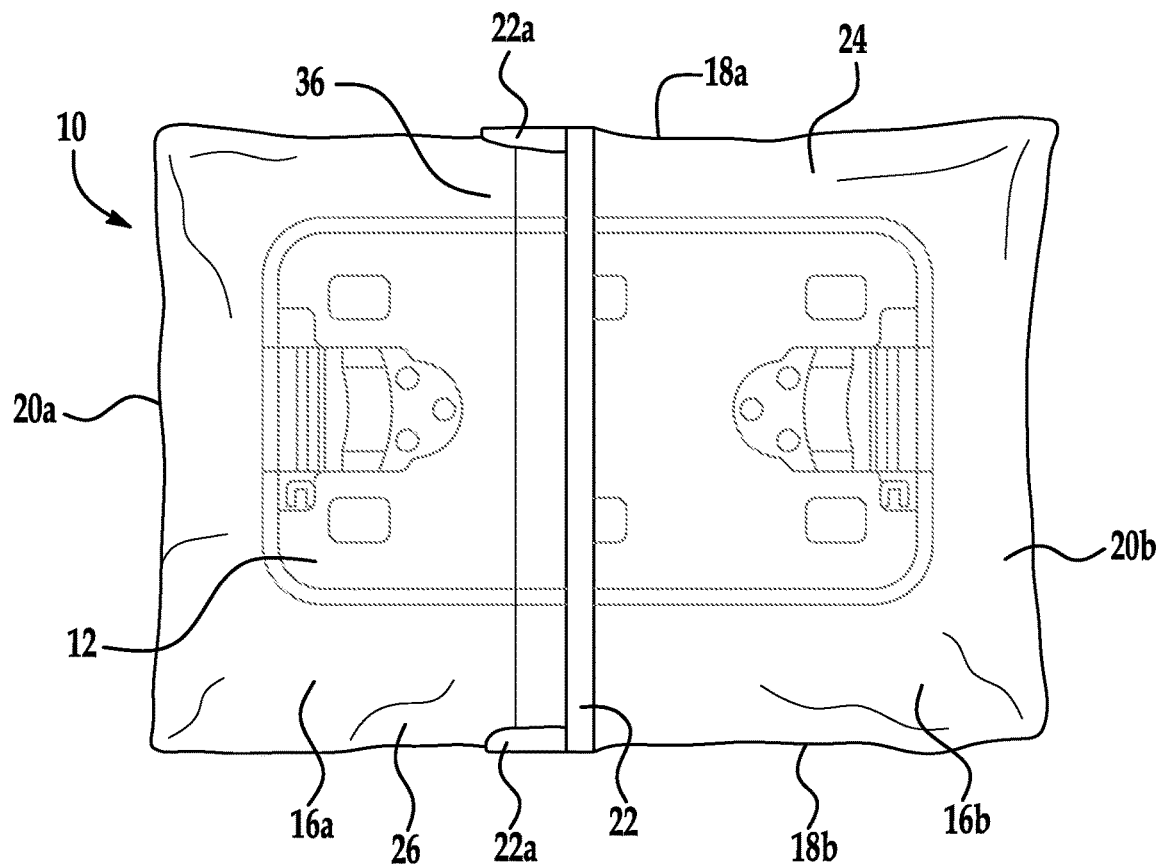
FIG. 1 is a top view of an exemplary pouch in accordance with the present invention, where a device is enclosed within the sealed pouch.

Embodiments of the present invention will now be described with reference to the drawings, wherein like reference numerals are used to refer to like elements throughout. It will be understood that the figures are not necessarily to scale.

A sterilization pouch in accordance with the present invention enables a user to easily open the pouch from a central region rather than from an end of the pouch. The opening region can be part of a pre-formed opening means that provides a region adjacent to a peal-open seam for the user to grasp. The opening features may be composed of materials that can be sealed in a manner that the seal remains closed when the pouch is subjected to normal handling, and yet can be opened easily without compromising aseptic presentation.

For example, a first portion of the pouch may be formed from a fibrous material, such as paper or Tyvek® plastic sheet, which enables sterilization medium to pass there through. The fibrous material may be formed from an uncoated fibrous material, or any breathable material that is impervious to microorganisms but pervious to gases. The remaining portion of the pouch may be formed from a thin non-fibrous or fibrous (coated or uncoated) plastic sheet material and bonded to the first portion along the outer peripheral edges to define an interior space. The pouch includes an opening means located in the central region of the pouch, the region formed as two pieces. Each piece can be grasped by one hand and pulled in opposite directions, thereby opening the pouch. The opening means may include finger holes to assist the user in grasping each piece of the opening means.

Figure 2:
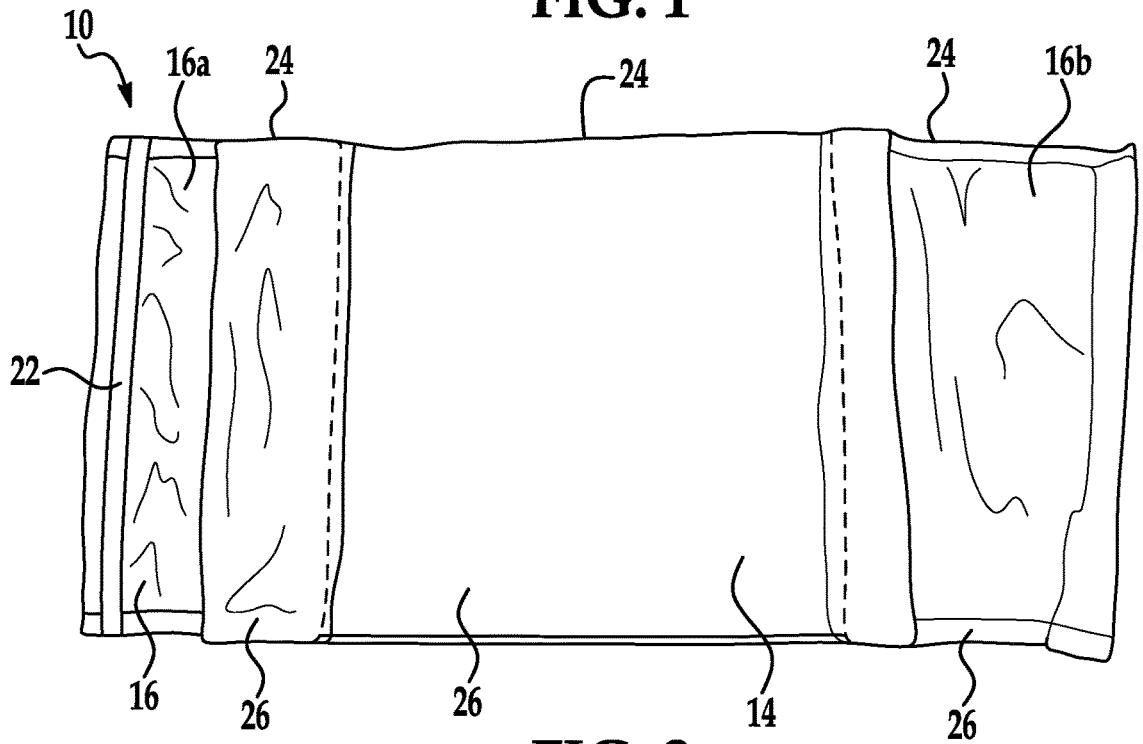
FIG. 2 is a top view of the pouch of FIG. 1 opened and the device stored therein removed.

Referring now to FIGS. 1 and 2, illustrated is an exemplary pouch 10 in accordance with an embodiment of the invention. In FIG. 1, the pouch 10 is shown in a sealed state with a device 12 stored inside the pouch 10. In the illustrated embodiment, the pouch 10 is formed from two sheets 14 (top sheet in FIG. 1), 16 (bottom sheet in FIG. 2), the first sheet 14 being "breathable" and the second sheet 16 being a non-breathable flexible film (e.g., a bilayer laminate plastic film, such as a polyethylene terephthalatepoly (PET) film laminated to polypropylene film or like material in which one film is fusible to the other). It should be appreciated, however, that the two sheets 14, 16 may be formed from the same material, e.g., both sheets may be formed from a breathable material or, if not used in a sterilization application, both sheets may be formed from a non-breathable material. Outer peripheral edges 18*a*, 18*b*, 20*a*, 20*b* of the sheets 14, 16 are joined together to define a pouch having an interior space for receiving the article 12. The peripheral edges may be joined by a heat seal, an adhesive, an adhesive tape, or any other suitable means for joining the sheets. It is noted that while two sheets are illustrated as forming the pouch, it could be formed from a single sheet folded upon itself and sealed along the peripheral edges.

With continued reference to FIGS. 1 and 2, a first releasable seam 22 spans between the first peripheral edge 18*a* of the sheet 16 to a second, opposite, peripheral edge 18*b* of the sheet 16. As can be seen in FIG. 1, the first releasable seam 22 divides the sheet 16 into a first sheet part 16*a* and a second sheet part 16*b*. Extension tabs 22*a* may be formed at ends of the first releasable seam to facilitate separation/grasping of the two layers. A second releasable seam 24 and a third releasable seam 26 each substantially span from a third peripheral edge 20*a* of the sheet to a fourth, opposite, peripheral edge 20*b* of the sheet and along the first peripheral edge 18*a* and the second peripheral edge 18*b*, respectively. As used herein, the term "substantially span" is defined as the seam spanning at least 70% of the length of the peripheral edge along which the seam is arranged, and more preferably at least 90% of the length of the peripheral edge along which the same is arranged. The second and third releasable seams 24, 26 are arranged generally perpendicular to the first releasable seam 22 (90 degrees, ±10 degrees). The first, second and third releasable seams 22, 24, 26 may include a heat-sealed portion, an adhesive tape portion, an adhesive portion, a fibrous portion, and/or a paper portion.

In one embodiment, the releasable seam 22 may include paper, fibrous (or like) strips, and small strips extending to the sides of the opening means. The paper or fibrous strips enable a heat seal to be formed between two plastic film sections, where the heat sealed portion can be easily be pulled apart. In contrast to the seam 22, the seams 24 and 26 may be formed by heat sealing the plastic film directly to the paper/fibrous material. As force is applied to the respective pieces to open the pouch 10, the paper or fibrous portion of the opening means easily shears and the respective sheets 16*a*, 16*b* are drawn in opposite directions. The result is that the pouch 10 is completely opened without any further manipulation of the pouch, thereby enabling a sterile user to remove the article 12 from the pouch 10 without exterior surfaces of the pouch contacting the article (see FIG. 2).

Figure 3:
FIG. 3 is a side view of an exemplary seam construction that can be used in the pouch in accordance with the invention.

Referring briefly to FIG. 3, illustrated is a side view of an exemplary releasable seam configuration that may be used for the first releasable seam 22. The exemplary releasable seam of FIG. 3 includes a layer of fibrous material 28 (e.g., Tyvek® plastic sheet) arranged between two layers 30, 32 of non-fibrous plastic film. The fibrous material 28 may be bonded to the layers 30, 32, and upon application of a force the fibrous material 28 shears, thus opening the seam.

Figure 4A:
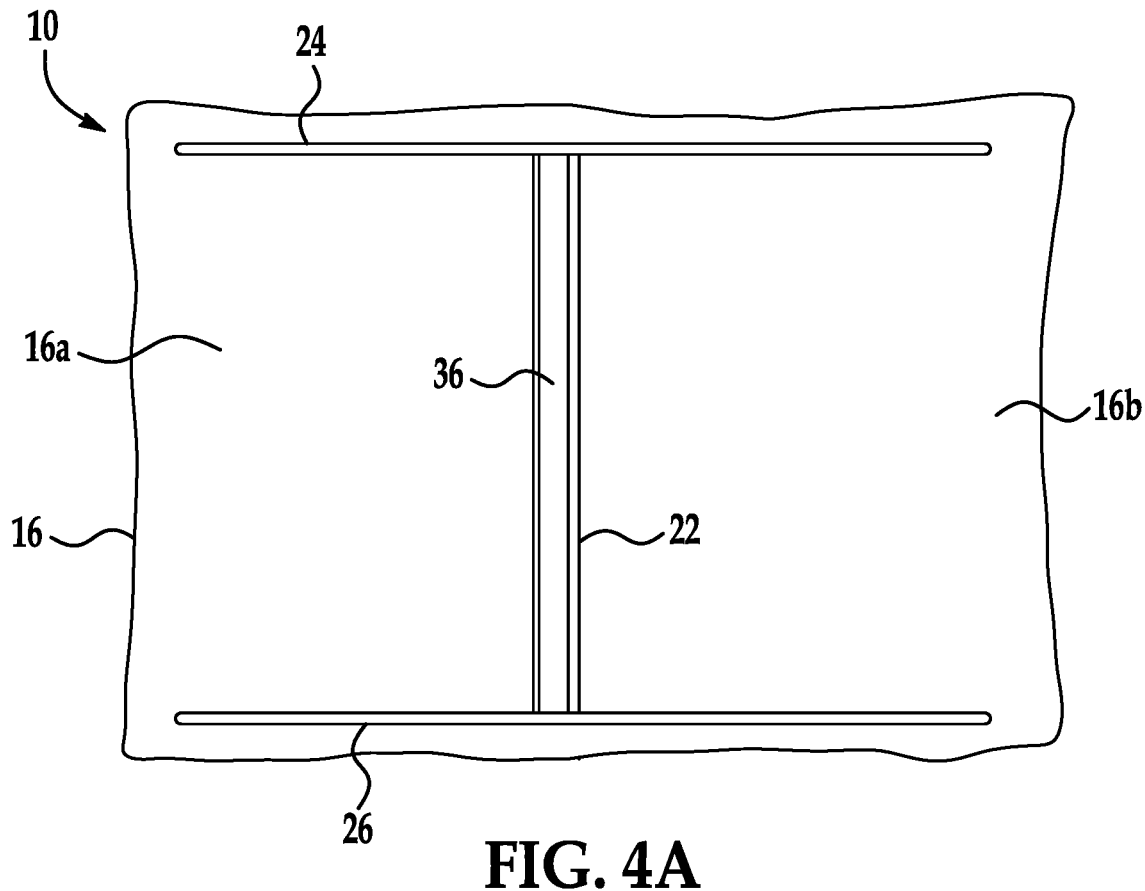
FIG. 4A is a top view of another exemplary pouch in accordance with the invention, the pouch including a zip-lock seal.
Figure 4B:
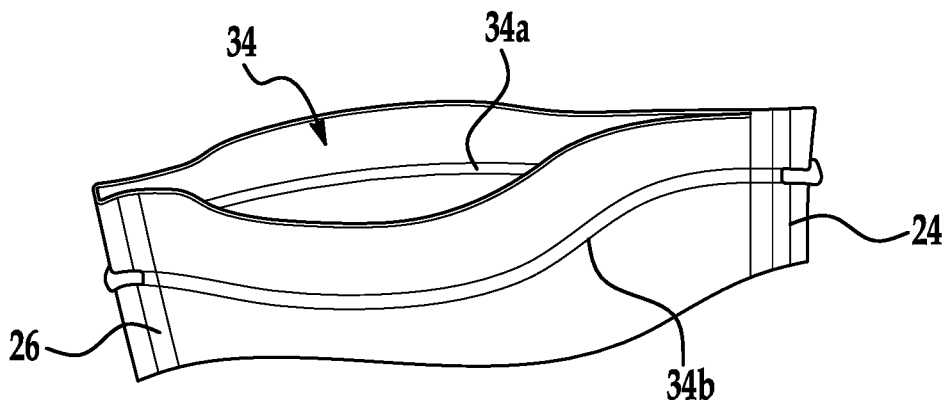
FIG. 4B illustrates the zip-lock seal of FIG. 4A in the open state.

Referring briefly to FIGS. 4A and 4B, in another embodiment the first, second and third releasable seams 22, 24, 26 may be formed as a zip-lock seam 34 having a mating male rib 34*a* and a female sealing closure 34*b*. As the male rib 34*a* is pressed against the female sealing closure 34*b*, the two portions lock together and form an air-tight seal. An advantage of the embodiment of FIGS. 4A and 4B is that the seal would be easy to open and close, and there would be no requirement for a heat sealer.

Regardless of the specific implementation, the first, second and third releasable seams 22, 24, 26 enable the pouch 10 to be completely opened such that the device 12 can be removed from the pouch 10 with reduced risk of contacting non-sterile portions (e.g., the outer portions) of the pouch. For example, once the pouch 10 is opened the device 12 stored therein can simply be lifted straight up, thus reducing the risk of contacting any outer (nonsterile) portions of the pouch 10.

To assist the user in opening the pouch, grasping portions 36 may be formed on or near one or more of the releasable seams to enable the user to pull apart the seam. For example, one side of the first releasable seam 22 may include additional material that extends beyond the seam, e.g., where the two sheets overlap but are not joined. This overlap potion enables a user to individually grasp each sheet part 16*a*, 16*b* and pull them apart, thereby splitting the seams. Alternatively, the grasping portions may be formed as loops or holes. A user then can place his/her fingers through the loops/hoes and pull the sheets apart.

Figure 5:
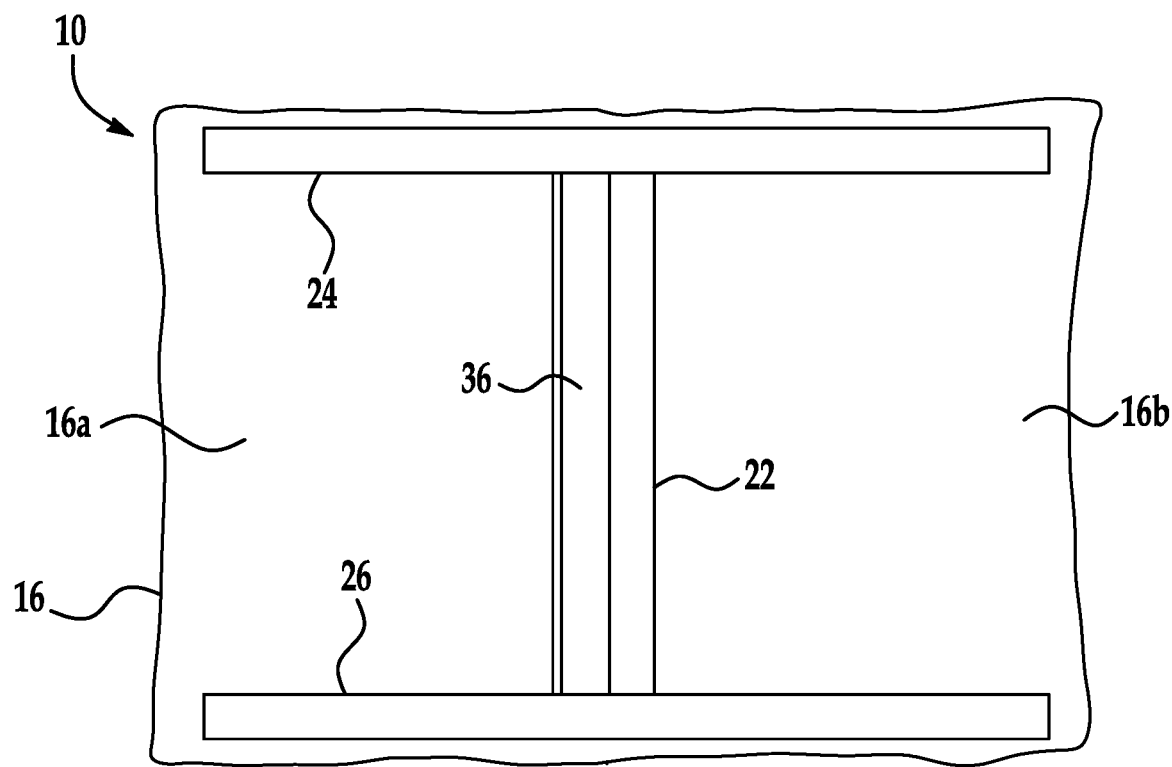
FIG. 5 is a top view of the exemplary pouch in accordance with the invention, where the seal divides one sheet of the pouch into two equal portions.
Figure 6:
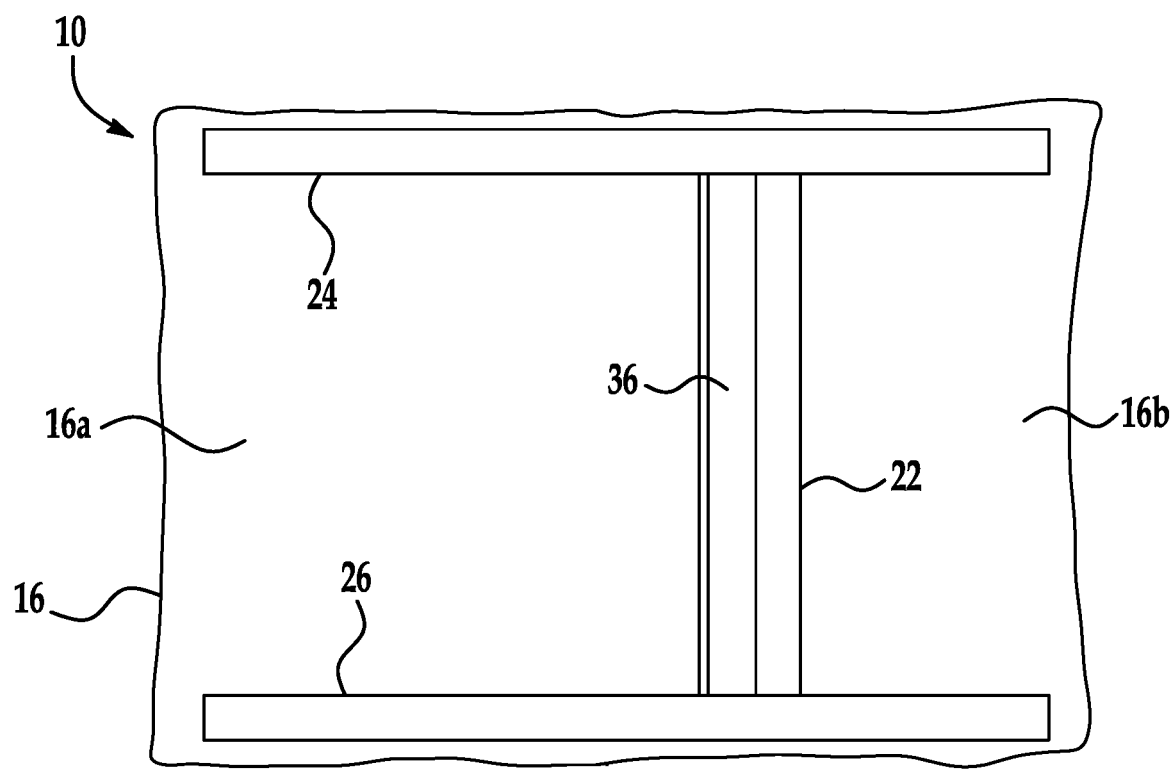
FIG. 6 is a top view of the exemplary pouch in accordance with the invention, where the seal divides one sheet of the pouch into two unequal portions.

While it is preferred that the first seam 22 is arranged along a central portion of the sheet, it could be shifted off center so long as it is not at the ends of the pouch. FIG. 5 illustrates an embodiment in which the first releasable seam 22 bisects sheet 16 such that the first sheet part 16*a* and the second sheet part 16*b* have approximately the same surface area, where approximately the same surface area means the surface area of the respective sheet parts are within 10 percent of each other. FIG. 6 illustrates an embodiment in which the first releasable seam 22 divides the sheet 16 into unequal parts. For example, a surface area of the first sheet part 16*a* is at least one third of a surface area of the second sheet part.

Figure 7A:
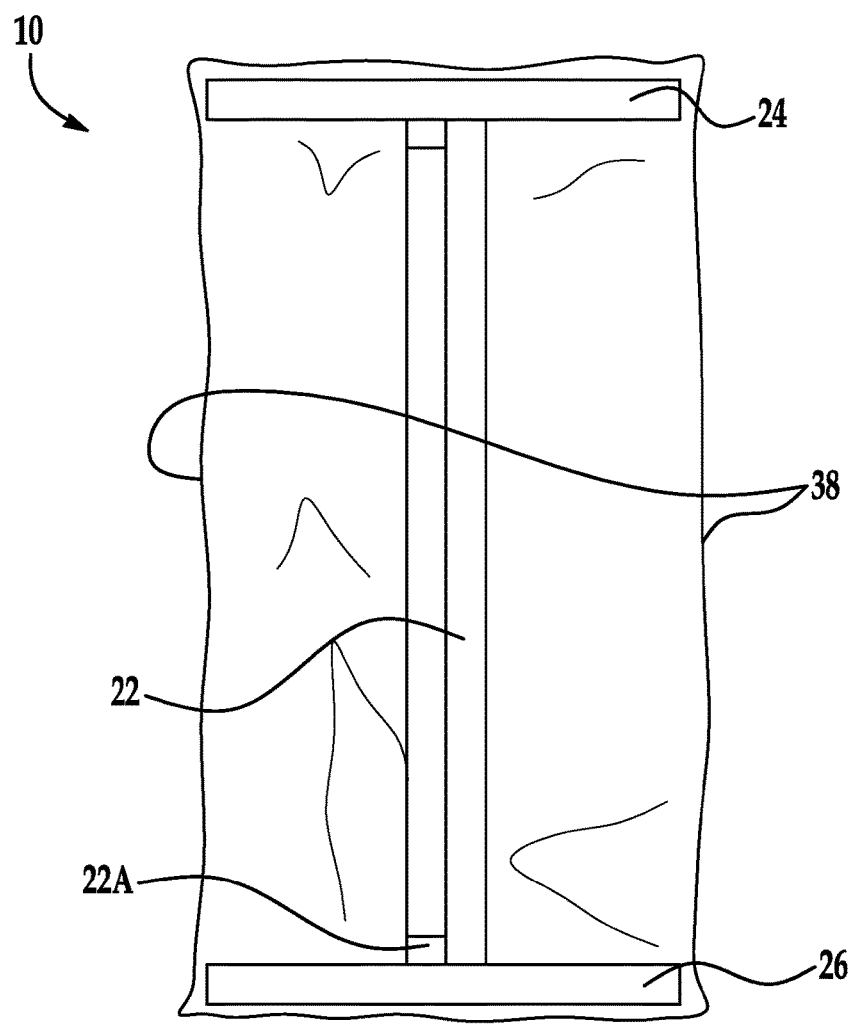
FIGS. 7A and 7B are top and perspective views of an exemplary pouch in accordance with the invention showing gussets.
Figure 7B:
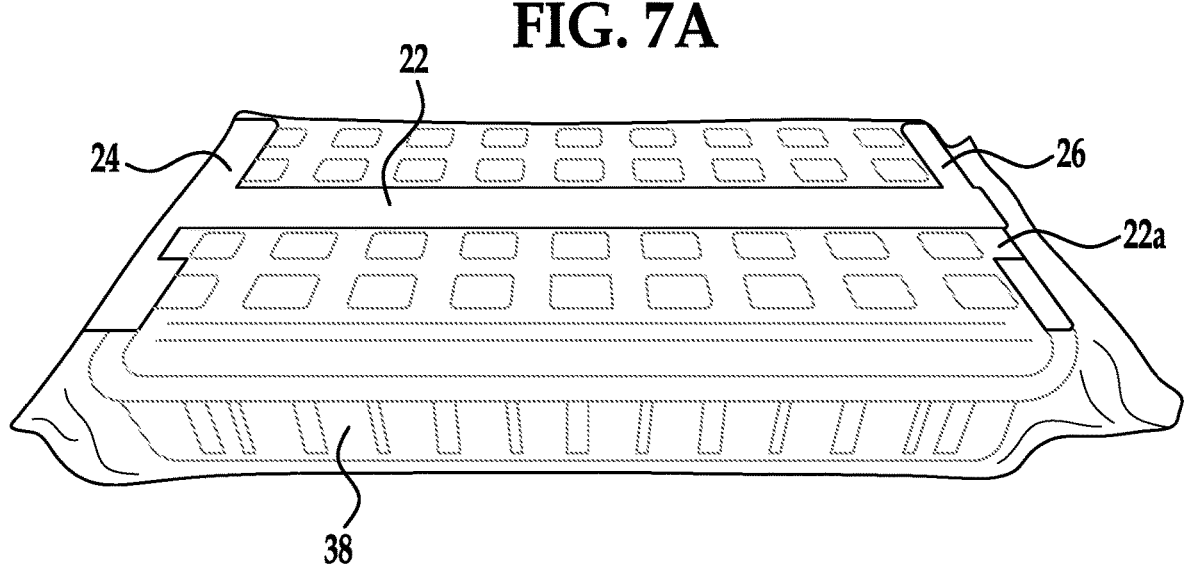
Figure 8:
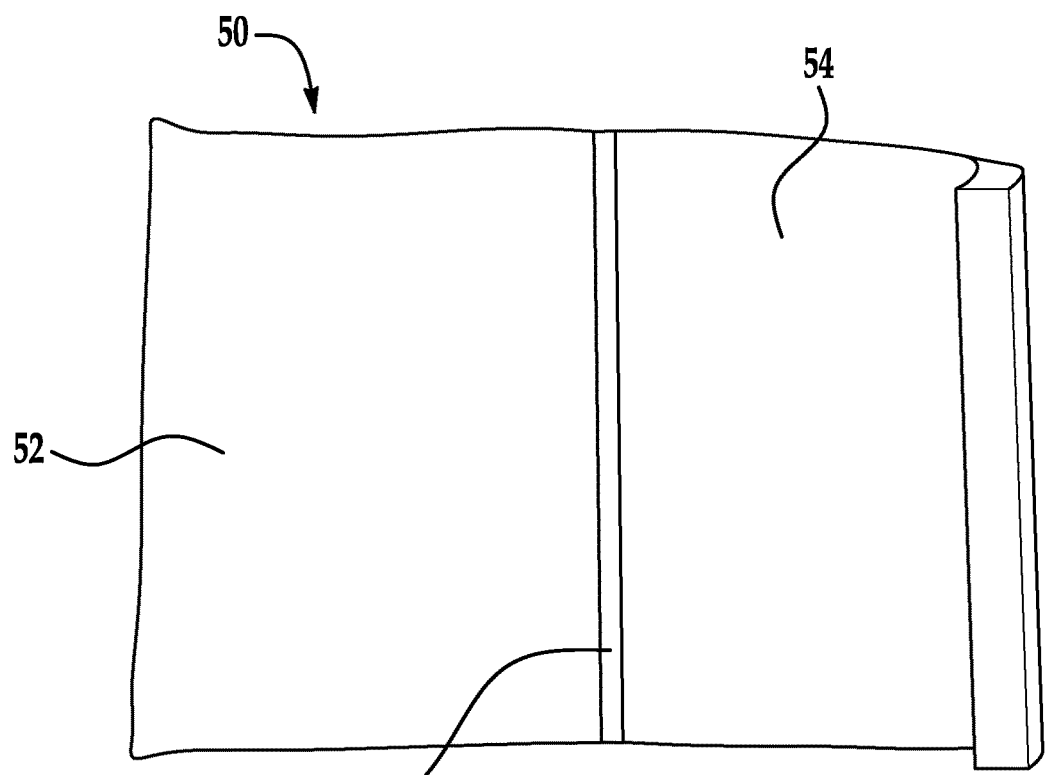
FIGS. 8-12 illustrate a method of forming a pouch according to one embodiment of the invention.
Figure 9:
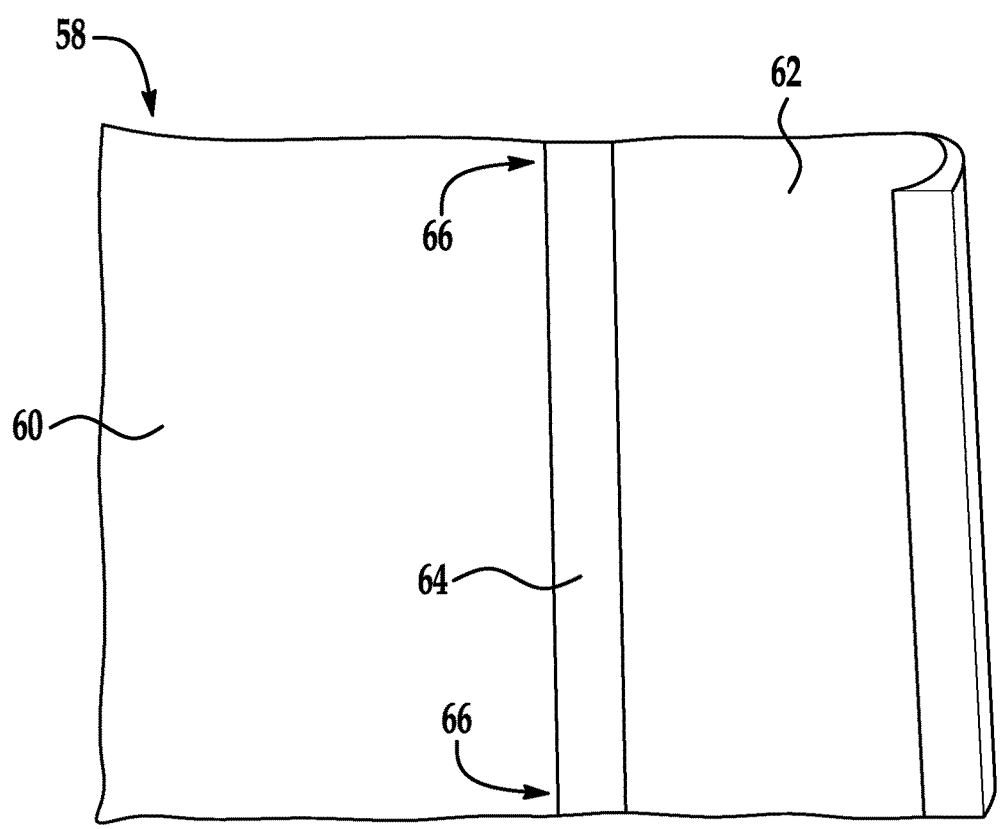
Figure 10:
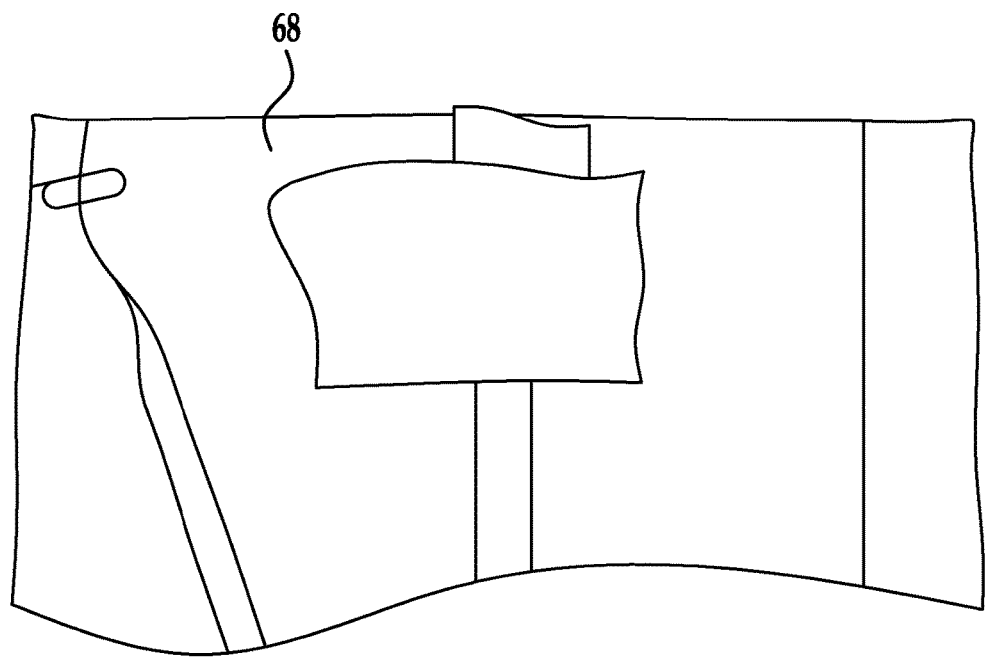
Figure 11:
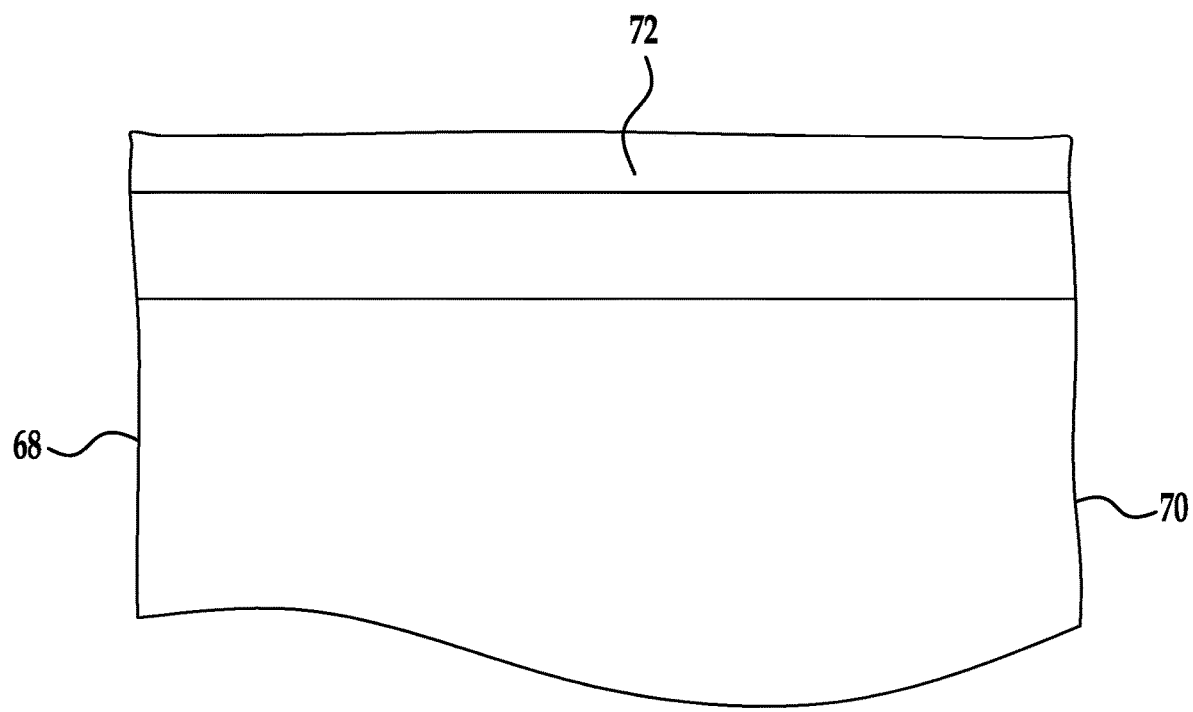
Figure 12:
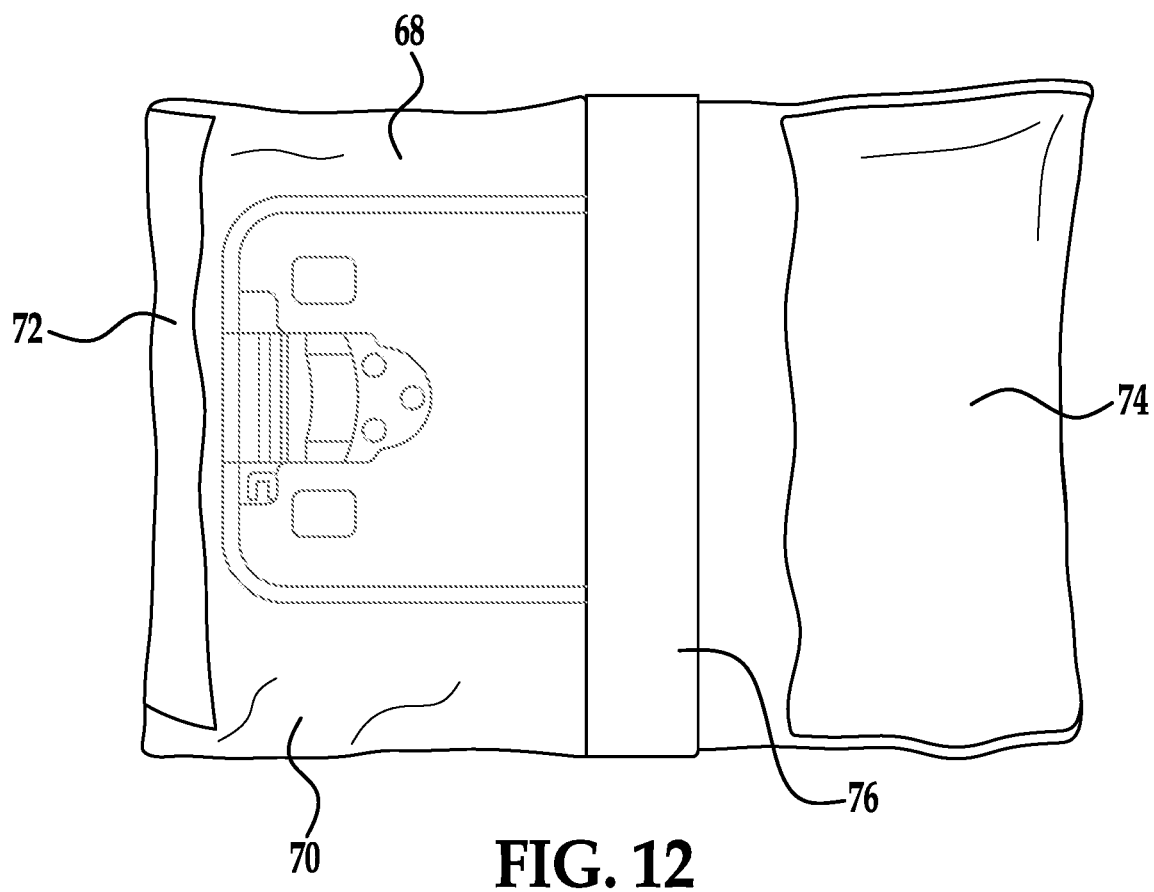

To provide a pouch having an interior space that is sufficiently large for oversized devices, gussets 38 may be included in the pouch, as shown in FIGS. 7A and 7B. When the pouch is fully collapsed, the overall footprint of the pouch is minimum. However, when needed the gussets can expand the size of the pouch to accommodate larger articles.

By way of example, one way to achieve closure of the pouch in accordance with the invention is to use 7.9 mil uncoated fibrous sheet (e.g., 1073B Tyvek® plastic sheet) and 48 gauge polyethylene terephthalate (PET, clear) laminated to 2 mil low density polyethylene (LDPE), plastic film. The pouch layers can be designed so that one part of the bottom is composed of the fibrous sheet and the other part of a heat sealable plastic film. The top fibrous sheet to plastic film seal has approximately a one inch overhang that can form the grasping region.

The top and bottom layers are aligned so that the bottom fibrous sheet portion is joined to the top portion's plastic sheeting and the bottom plastic sheeting is aligned with the top fibrous sheet. The seams of the top and bottom, where the two materials are joined, should be properly aligned to provide a uniform seal with no channel to allow microbial ingress. The edge can be heat sealed, and the parallel edge is formed in the same manner. The two sides of the area designed to be grasped when opening are heat sealed to each other at both edges of the pouch. The user peals this joined area to free the two sides prior to opening the pouch.

The third edge also can be heat sealed. In this regard, the plastic film may extend beyond the fibrous sheet and is folded over to form a heat seal to the fibrous sheet on both sides (plastic sheet, fibrous sheet, and plastic sheet). The three layers may provide additional strength to the pouch 10. Alternatively, the seal may also be a standard two-layer heat seal. A device, such as a tray, can be placed inside the pouch and the fourth edge is sealed. To open the pouch the user grasps the opening feature (one side fibrous sheet and the other side plastic film) and peals open the seal and along the side seams.

Another way to achieve closure of the pouch in accordance with the invention is to form the opening seal as a three-layer construct. This can include a thin fibrous sheet strip sandwiched between two layers of the plastic film, and a heat seal can be formed between the three layers. The formed plastic film layer with opening feature is placed onto the fibrous sheet layer and tabs of fibrous sheet are placed between the plastic opening flaps. The sides of the pouch 10 can be heat sealed. Additional fibrous sheet tabs can be heat sealed to the plastic opening flaps at the center to facilitate separating the two layers of plastic. One end of the pouch is heat sealed, the tray is placed into the pouch 10 and the last end is heat sealed. The opening feature is positioned at the center of the pouch. The user opens the pouch by grasping the opening feature and pealing the layers apart.

Described now is a method of making a pouch in accordance with the present invention, With reference to FIGS. 8-12, according to one embodiment of making the pouch 10 a bottom sheet 50 is formed by joining a breathable layer 52 (e.g., paper, Tyvek® plastic sheet, or other breathable material) to a plastic film layer 54 along one edge 56. The edge 56 joining the two layers may be formed via a heat seal, where the edge 56 is approximately along a center of the formed bottom sheet 50. A top sheet 58 is formed in a manner similar to that of the bottom sheet 50, where a breathable layer 60 is joined to a plastic film layer 62 via a heat seal along one edge 64, the edge 64 formed along a central region of the top sheet 58. The joined area of the top sheet 58 is heat sealed together to form grasping areas 66 that are capable of being pealed apart by a user and pulled in opposite directions. The bottom sheet 50 and the top sheet 58 then are placed adjacent to each other such that the breathable layer 52 of the bottom sheet 50 is adjacent to the plastic film layer 62 of the top sheet 58, and the plastic film layer 54 of the bottom sheet 50 is adjacent to the breathable layer 60 of the top sheet 58. In this regard, the top and bottom sheets 50, 58 are aligned such that the seams joining the two sheets along their respective edges meet without forming a gap, and a heat seal then is formed along the edges 68, 70. For a third edge 72, the plastic film layer 62 is extended beyond the breathable layer 52 and folded over and heat sealed such that a heat seal is formed on both sides of the breathable layer 52. Alternatively, a two layer seal similar to the seal along edges 68, 70 may be utilized along the edge 72. An article then is placed in the pouch via the remaining open end and the fourth edge 74 is heat sealed such that the opening feature 76 is located approximately in the center of the pouch.

Figure 13:
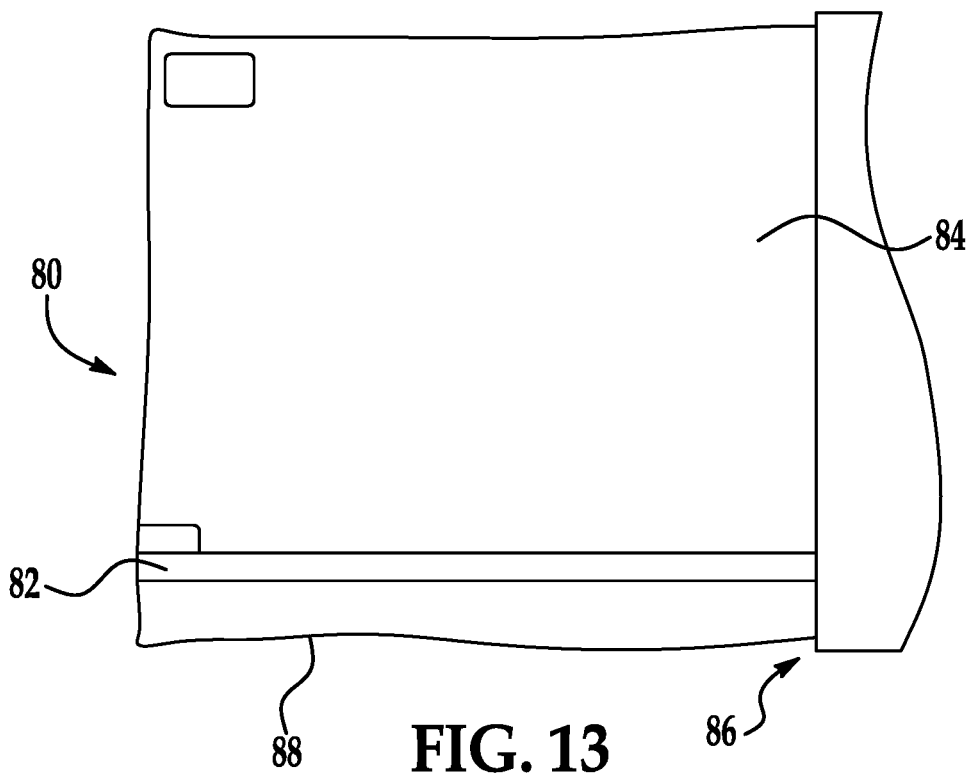
FIGS. 13-15 illustrate a method of forming a pouch according to another embodiment of the invention.
Figure 14:
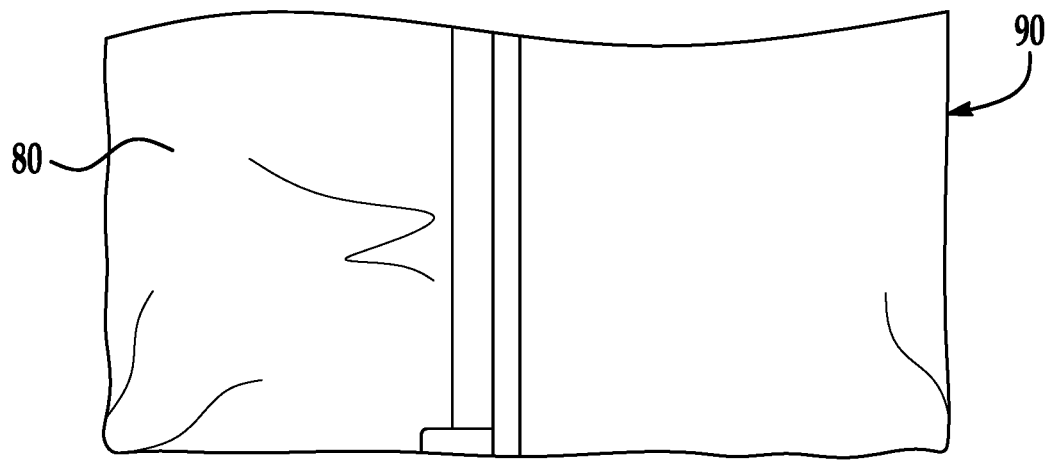
Figure 15:
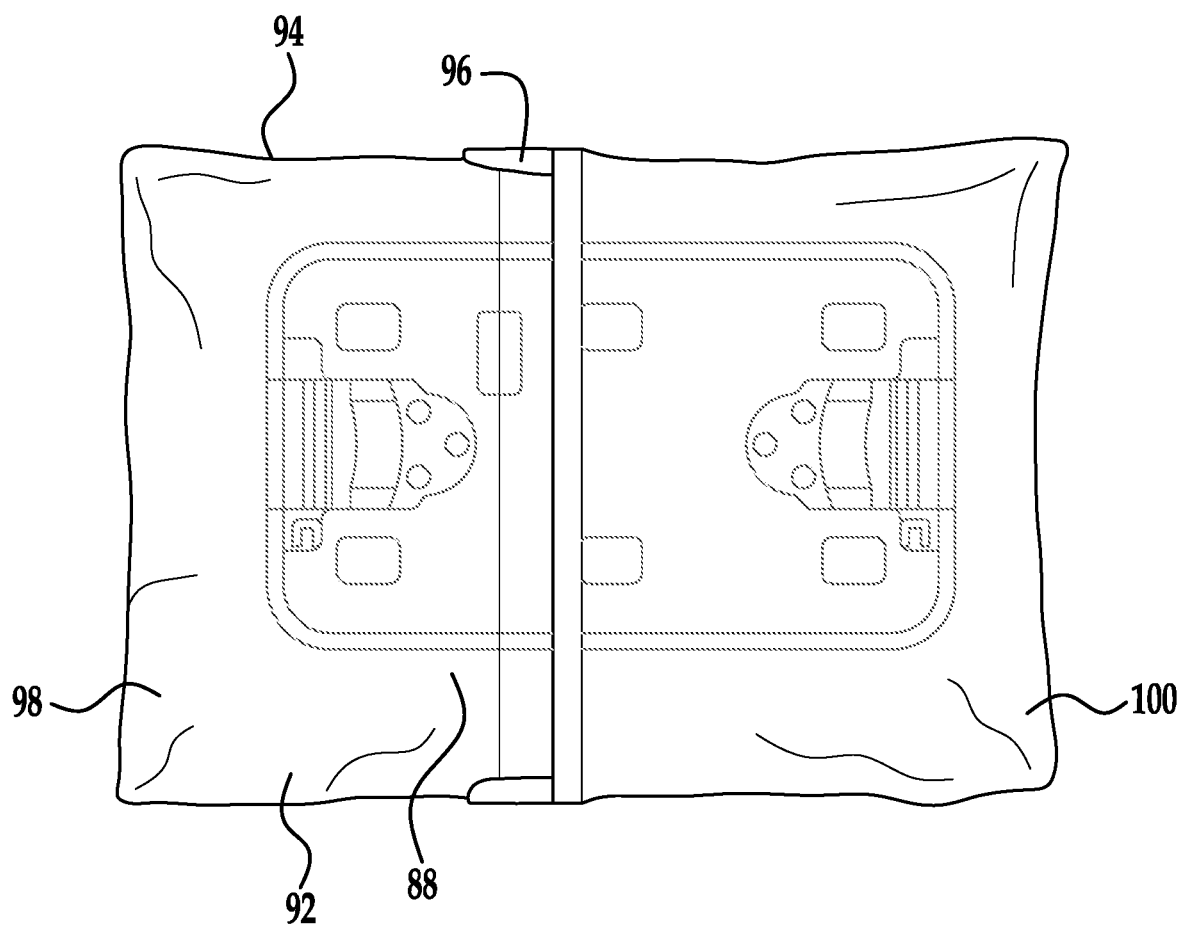

Referring now to FIGS. 13-15, according to another embodiment of making the pouch 10 a top sheet 80 is formed by placing a breathable and/or fibrous strip of material 82 between two layers of plastic film 84, 86. The combination of the strip 82 and two layers of plastic film 84, 86 then are heat sealed together along edges to define the top sheet 80 having an opening feature 88. The formed top sheet 80 then is placed over a breathable sheet 90 and the top and bottom side edges 92, 94 are heat sealed together. Strips 96 of fibrous material can be heat sealed into flaps of the opening feature 88 so that the two plastic layers of the opening feature 88 are easy to separate. The top and bottom sheets at one end edge 98 then are heat sealed and an article is placed in the pouch via the remaining open end. The edge 100 at the open end then is heat sealed.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

What is claimed is:

1. A sterilizable pouch comprising:
 a first sheet;
 a second sheet, wherein outer peripheral edges of the first and second sheets are sealed together to define a pouch having an interior space for receiving an article therein;
 a first releasable seam spanning between a first peripheral edge of the first sheet to a second, opposite, peripheral edge of the first sheet, the first releasable seam dividing the first sheet into a first sheet part and a second sheet part;
 a first flap portion attached to the first sheet and extending beyond the first releasable seam on an outer surface of the pouch;
 a second flap portion attached to the second sheet and extending beyond the first releasable seam on an outer surface of the pouch; and
 a second releasable seam and a third releasable seam each substantially spanning from a third peripheral edge of the first sheet to a fourth, opposite, peripheral edge of the first sheet and along the first peripheral edge and the second peripheral edge, respectively, the second and third releasable seams arranged generally perpendicular to the first releasable seam, where the first, second and third releasable seams enable the pouch to be completely opened such that a device can be removed from the pouch without the device contacting non-sterile portions of the pouch.

2. The sterilizable pouch according to claim 1, wherein the first and second sheets are joined together along outer peripheral edges of the respective sheets to define the pouch.

3. The sterilizable pouch according to claim 1, wherein the first and second sheet parts have approximately the same surface area.

4. The sterilizable pouch according to claim 1, wherein the first releasable seam bisects the first sheet.

5. The sterilizable pouch according to claim 1, wherein a surface area of the first sheet part is at least one third of a surface area of the second sheet part.

6. The sterilizable pouch according to claim 1, wherein at least one of the first sheet or the second sheet comprises a breathable material.

7. The sterilizable pouch according to claim 6, wherein the breathable material comprises a fibrous material.

8. The sterilizable pouch according to claim 7, wherein the fibrous material comprises an uncoated fibrous material.

9. The sterilizable pouch according to claim 6, wherein the breathable material is impervious to microorganisms and pervious to gases.

10. The sterilizable pouch according to claim 1, wherein at least one of the first, second or third releasable seam comprises a mating male rib and a female sealing closure.

11. The sterilizable pouch according to claim 1, wherein at least one of the first, second or third releasable seam comprises a paper seam.

12. The sterilizable pouch according to claim 1, wherein at least one of the first, second and third releasable seam comprises a layer of fibrous material arranged between two layers of plastic film.

13. The sterilizable pouch according to claim 1, wherein at least one of the first, second or third releasable seam comprises a heat-sealed portion.

14. The sterilizable pouch according to claim 1, wherein at least one of the first, second or third releasable seam comprises adhesive tape.

15. The sterilizable pouch according to claim 1, wherein one of the first sheet or the second sheet comprises a non-breathable flexible film.

16. The sterilizable pouch according to claim 15, wherein the non-breathable flexible film comprises low density polyethylene plastic.

17. The sterilizable pouch according to claim 1, wherein at least one of the second and third releasable seam comprises a grasping portion for pulling apart at least one of the first, second or third releasable seam.

18. The sterilizable pouch according tee claim 1, wherein the pouch comprises gussets.

19. The sterilizable pouch according to claim 1, wherein the first and second flaps comprise through holes.

20. A sterilizable pouch, comprising:
a first outer surface;
a second outer surface arranged opposite the first outer surface, the second outer surface joined to the first outer surface along peripheral edges of the first and second outer surfaces to define an interior space for storing an article;
a first releasable seam spanning between a first peripheral edge and a second peripheral edge of one of the first outer surface or the second outer surface, the first releasable seam dividing one of the first outer surface or the second other surface into a first part and a second part, wherein a surface area of the first part and the second part are substantially equal to each other;
a first flap portion attached to the first outer surface and extending beyond the first releasable seam;
a second flap portion attached to the second outer surface and extending beyond the first releasable seam: and
at least one second releasable seam substantially spanning between a third peripheral edge and a fourth, opposite peripheral edge of one of the first outer surface or the second outer surface and along at least one of the first peripheral edge or the second peripheral edge, the at least one second releasable seam arranged generally perpendicular to the first releasable seam,
where the first and at least one second releasable seams enable the pouch to be completely opened such that an article stored in the interior space can be removed without the device contacting non-sterile portions first or second outer surfaces.

21. A sterilizable pouch comprising:
at least one sheet, wherein outer peripheral edges of the at least one sheet are sealed together to define a pouch having an interior space for receiving an article therein;
a first releasable seam spanning between a first peripheral edge of the at least one sheet to a second, opposite, peripheral edge of the at least one sheet, the first releasable seam dividing the at least one sheet into a first sheet part and a second sheet part;
a first flap portion attached to a first end of the at least one sheet and extending beyond the first releasable seam on an outer surface of the pouch;
a second flap portion attached to a second end of the at least one sheet and extending beyond the first releasable seam on an outer surface of the pouch; and
a second releasable seam and a third releasable seam each substantially spanning from a third peripheral edge of the at least one sheet to a fourth, opposite, peripheral edge of the at least one sheet and along the first peripheral edge and the second peripheral edge, respectively, the second and third releasable seams arranged generally perpendicular to the first releasable seam, where the first, second and third releasable seams enable the pouch to be completely opened such that a device can be removed from the pouch without the device contacting non-sterile portions of the pouch.

* * * * *